(12) United States Patent
Castrén et al.

(10) Patent No.: US 8,133,906 B2
(45) Date of Patent: Mar. 13, 2012

(54) METHOD OF TREATING AMBLYOPIA

(75) Inventors: Eero Castrén, Helsinki (FI); Lamberto Maffei, Pisa (IT); Jose Maya Vetencourt, Pisa (IT)

(73) Assignee: Hermo Pharma Oy, Helsinki (FI)

( * ) Notice: Subject to any disclaimer, the term of this patent is extended or adjusted under 35 U.S.C. 154(b) by 14 days.

(21) Appl. No.: 12/306,798

(22) PCT Filed: Jun. 27, 2008

(86) PCT No.: PCT/FI2008/050392
§ 371 (c)(1),
(2), (4) Date: Apr. 10, 2009

(87) PCT Pub. No.: WO2009/004114
PCT Pub. Date: Jan. 8, 2009

(65) Prior Publication Data
US 2010/0093805 A1   Apr. 15, 2010

(30) Foreign Application Priority Data
Jun. 29, 2007 (FI) .................................. 20075498

(51) Int. Cl.
*A61K 31/44* (2006.01)
*A61K 31/34* (2006.01)
*A61K 31/135* (2006.01)

(52) U.S. Cl. .................... 514/338; 514/469; 514/647

(58) Field of Classification Search ............... 514/338, 514/469, 647
See application file for complete search history.

(56) References Cited

U.S. PATENT DOCUMENTS

| 5,567,731 A | 10/1996 | Laties et al. |
| 5,571,823 A | 11/1996 | Stone et al. |
| 6,319,953 B1 * | 11/2001 | Carlson et al. ............... 514/649 |
| 6,692,481 B2 * | 2/2004 | Guerrero .................. 604/521 |
| 6,876,758 B1 * | 4/2005 | Polat et al. .................. 382/128 |
| 2003/0114830 A1 | 6/2003 | Guerrero |

FOREIGN PATENT DOCUMENTS

| WO | WO-94/25034 A1 | 11/1994 |
| WO | WO-01/52832 A1 | 7/2001 |
| WO | WO-03/032975 A1 | 4/2003 |

OTHER PUBLICATIONS

Baldessarini RJ, Chapter 19 Drugs and the Treatment of Psychiatric Disorders—Depression and Anxiety Disorders, "Goodman & Gilman's The Pharmacological Basis of Therapeutics, 10th ed." Hardman JG, Limbird LE, and Gilman AG, Eds., McGraw-Hill, 2001, 447-484 (p. 457 provided).*
Packwood EA, Cruz OA, Rychwalski PJ, Keech RV. The psychosocial effects of amblyopia study. J AAPOS. Feb. 1999;3(1):15-7.*
Vetencourt, M. et al., "The Antidepressant Fluoxetine Restores Plasticity in the Adult Visual Cortex", www.sciencemag.org, Science, vol. 320, 2008, pp. 385-387.
Castren, "Neurotrophic effects of antidepressant drugs", Current Opinion in Pharmacology, 2004, vol. 4, pp. 58-64, XP-002582489.
Galuske et al., Differential effects of neurotrophins on ocular dominance plasticity in developing and adult cat visual cortex, European Journal of Neuroscience , vol. 12, 2000, pp. 3315-3330, XP-002582487.
Hata et al., "Brain-Drived Neurotrophic Factor Expands Ocular Dominance Columns in Visual Cortex in Monocularly Deprived and Nondeprived Kittens But Does Not in Adult Cats", The Journal of Neuroscience, 2000, vol. 20, No. RC57, pp. 1-5, XP-002582488.
Sale et al., "Environment enrichment in adulthood promotes amblyopia recovery through a reduction of intracortical inhibition", Nature Neuroscience, vol. 10, No. 6, Jun. 2007, pp. 679-681, XP-002582486.

* cited by examiner

*Primary Examiner* — San-Ming Hui
*Assistant Examiner* — Paul Zarek
(74) *Attorney, Agent, or Firm* — Birch, Stewart, Kolasch & Birch, LLP (57) ABSTRACT

The present invention relates to a method of treating or alleviating the symptoms of amblyopia. It is based on the discovery that repeated administration of a specific drug, which is known to be clinically active to treat depression in humans, results in improved vision of the amblyopic eye.

14 Claims, 3 Drawing Sheets

METHOD OF TREATING AMBLYOPIA

INTRODUCTION

Amblyopia, a condition where a vision in one eye is impaired due to insufficient use of that eye during development, is a common disorder in adults without any treatment. The present invention relates to a method of treating or alleviating the symptoms of amblyopia. It is based, in part, on the discovery that repeated administration of a specific drug, which is known to be clinically active to treat depression in humans (antidepressant drug) results in the improved vision of the amblyopic eye in experimental animals through an increase in the expression of brain-derived neurotrophic factor (BDNF) and reduced cortical inhibition.

BACKGROUND OF THE INVENTION

Amblyopia

Amblyopia is a clinical condition which is characterized by a dysfunction in the processing of visual information. Typically, it is detected as reduced visual acuity in the absence of pathological findings in the opthalmological examination. Amblyopia results from abnormal processing of visual information in the visual cortex due to reduced or imbalanced use of eyes during a critical period of postnatal development. Most often, strabismus, anisomeropia or visual deprivation in one eye during the first years leads to permanent reduction in vision acuity in the affected eye (Holmes and Clarke, 2006). Amblyopia is the most common cause of monocular vision loss with the prevalence in children of 1-5% and in adults about 3% (Holmes and Clarke, 2006). Adult amblyopics show impaired depth perception due to the lack of stereovision and are at a significantly increased risk of blindness if vision in the better eye is lost due to accident or disease. Amblyopia can be prevented if the use of the weaker eye is encouraged during childhood by optical or pharmaceutical occlusion of the better eye. However, occlusion therapy only works during a critical period of postnatal development; after the gradual closure of the critical period in adolescence, in humans typically by the age of 10 years, occlusion no longer helps and amblyopia remains permanent.

Experimental research using experimental animals, such as monkeys, cats, rats and mice has over several decades revealed the neurobiological processes underlying amblyopia (Berardi et al., 2003). During early postnatal development, inputs from left and right eye compete for the innervation of the visual cortex and in the case of normal vision in both eyes, the mammalian visual cortex organises into eye-specific columns known as ocular dominant (OD) columns, which represent morphological and functional segregation of inputs from each eye into the layer IV of the primary visual cortex. The proper innervation of the visual cortex requires balanced visual input through both eyes (Berardi et al., 2003). Hence, if the other eye is closed during the early postnatal development and kept closed to adulthood, the open eye takes over the deprived eye and gradually innervates almost the entire primary visual cortex, while the deprived eye looses its connectivity with the neurons in the visual cortex both anatomically and physiologically. This reorganization takes place most effectively during a critical period during the postnatal development, which lasts for between a few days to few years, depending on the species and leads to the greatly impaired visual acuity of the deprived eye (Berardi et al., 2003). After the closure of the critical period, in adulthood, closure of the other eye will not significantly affect the visual acuity of the closed eye and the already established anatomical and physiological segregation into OD columns in the brain and, conversely, an eye deprived during the critical period will not improve its visual acuity or regain the lost anatomical or physiological connectivity, if opened in adulthood. It has been demonstrated that the increase and maturation of the gamma-aminobutyric acid (GABA)-mediated neuronal inhibition in the visual cortex is a critical factor which brings about the closure of the critical period during development (Berardi et al., 2003). In conclusion, even though amblyopia develops as a consequence of a problem in the eye (strabismus, anisomeropia or visual deprivation), after the end of the critical period amblyopia is no longer an eye problem, it is a problem of the neuronal connections between the eye and the visual cortex. Any measures which correct the underlying developmental problem in the eye (such as operative treatment of strabismus) after the closure of the critical period, have not been shown to improve the visual acuity of the amblyopic eye.

Currently, there are no pharmacological interventions which could help to regain or improve vision in the deprived eye in adulthood, after the closure of the critical period (Holmes and Clarke, 2006). Occasional open-label clinical trials with L-DOPA and Citocholine have suggested that pharmacological treatments might improve vision in adult amblyopics (Campos and Fresina, 2006), but the side effects of these drugs have prevented their use. Methods have been proposed where the pharmacological agents are used to influence the growth of eyes during development; abnormal eye growth during early development may produce anisomeropia and therefore lead to the development of amblyopia (WO 9425034 A1; WO 0152832 A1; WO 03032975 A1; U.S. Pat. Nos. 5,567,731 A; 5,571,823 A; US 2003114830 A1). However, since amblyopia is a disorder of the connectivity between the eye and the brain, any means which influences eye growth will not ameliorate the lost neuronal connectivity of the amblyopic eye in the visual cortex after the closure of the critical period. Intracortical injection of an enzyme (Chondroitinase ABC), which degrades extracellular matrix has been shown to reinstate critical period plasticity in adult rat brain, but the enzyme needs to be injected at several locations directly into the visual cortex (Pizzorusso et al., 2002; Pizzorusso et al., 2006). A treatment which could improve the vision in the amblyopic eye in adulthood would be very welcome, in particular in those cases where the vision of the better eye is lost after the closure of the critical period.

Antidepressant Drugs

Drugs which are clinically used to treat symptoms of depression and mood disorders in humans are called antidepressant drugs or antidepressants. Most of the clinically active antidepressants increase the synaptic concentrations of monoamine transporters serotonin (5-hydroxytryptamine, 5-HT) or norepinephrine (NE) by either inhibiting their reuptake into cells (reuptake inhibitors) or by inhibiting monoamine oxidase (MAO), which degrades these transmitters (monoamine oxidase inhibitors, MAOI). Reuptake inhibitors are subdivided into tricyclic antidepressants, serotonin selective reuptake inhibitors (SSRI) and NE-selective reuptake inhibitors (NSRI). Serotonin-norepinephrine reuptake inhibitors (SNRIs) inhibit the reuptake of both serotonin and norepinephrine into cells. Among antidepressants, the SSRIs are the most widely used drug class, largely due to the fact that they produce relatively few side effects. Among the SSRIs, fluoxetine is one of the most widely used drugs. Clinical experience of over 50 years indicates that all known antidepressant drugs need to be administered repeatedly over a period of at least several weeks for the clinical efficacy.

Antidepressants and Neuronal Plasticity

Neuronal plasticity refers to the ability of neurons to modify their connectivity by either forming new neurons or synaptic contacts or withdrawing existing contacts, or by potentiating or depressing the strength of the existing synaptic contacts. The neurotrophic factor Brain-derived neurotrophic factor (BDNF) is a critical regulator of neuronal plasticity in both developing and adult brain. Evidence accumulated over the last decade suggests that antidepressant drugs are involved in the regulation of neuronal plasticity (Castrén, 2004). Antidepressant drugs increase the production of new neurons in the hippocampal dentate gyrus and increase axonal sprouting and synaptogenesis in hippocampus. Antidepressant treatments also increase the expression of plasticity-related genes and proteins in the hippocampus (Castrén, 2004). Specifically, representatives of all the known antidepressant classes increase the production of the mRNA for BDNF when administered repeatedly and activate the BDNF receptor trkB, as measured by increased trkB autophosphorylation, after either a single or repeated administration (Castrén, 2004). BDNF and its receptor trkB are critical mediators of neuronal plasticity and they also appear to be critical mediators of the efficacy of antidepressant drugs at least in rodents.

SUMMARY OF THE INVENTION

The object of the present invention is to provide a method for treating or alleviating amblyopia in humans who have passed the critical period of postnatal visual development.

Within this description, the term "a human having passed the critical period of postnatal visual development" is intended to mean all human beings (adolescents, adults) having passed the critical period of postnatal visual development. The closure of the critical period is gradual but typically in humans the critical period does not extend beyond the age of about 10 years.

Another object of the present invention is to provide amblyopia as a novel indication of use for antidepressant drugs, which already are accepted to human treatment in mood disorders. The invention is thus directed to the use of antidepressant drugs for the manufacture of a medicament for treating or alleviating amblyopia in humans who have passed the critical period of postnatal visual development.

A further object of the present invention is to provide a method for treating or alleviating amblyopia with compounds which increase BDNF or reduce GABA-mediated inhibition in the visual cortex.

Yet another object of the invention is to provide a method of treating amblyopia, wherein the drug treatment is combined with a rehabilitation treatment.

Within this description, the term "rehabilitation" is intended to mean any measures, which will support or encourage the use of the amblyopic eye. Rehabilitation may refer to, but is not limited to, physical (patching) or pharmacological occlusion of the vision in the better eye, or training programs which encourage the use of the amblyopic eye.

A further object of the invention is a method for treating or alleviating amblyopia in a human having passed the critical period of postnatal visual development, wherein said method comprises administering to the said human an effective amount of at least one drug demonstrated to increase the levels of BDNF (Brain-derived neurotrophic factor) in the cerebral cortex, preferably in combination with a rehabilitation treatment.

These and other objects are achieved by the present invention, in which it is shown that antidepressant drugs, specifically SSRIs and more specifically fluoxetine, can be used to treat amblyopia in mammals having passed the critical period of postnatal visual development.

DESCRIPTION OF THE FIGURES

FIG. 1. Amblyopia recovery in adulthood after repeated treatment with fluoxetine. (A) Restored plasticity in the adult visual cortex. Monocular deprivation (MD) in fluoxetine treated adult rats induced an ocular dominance (OD) shift of visual cortical neurons in favour of the non deprived eye (C/I VEP ratio 1.0±0.08 t-test p<0.001 n=5) but not in control animals (C/I VEP ratio 2.73±0.2 n=5). (B-C) Visual acuity (VA) recovery in adult amblyopic rats repeatedly treated with fluoxetine. Electrophysiological (B) and behavioral (C) assessment of VA of the formerly deprived eye, which was lower than that of the fellow eye in control animals (paired t-test p<0.001 for a and p<0.001 for b n=5) but not in fluoxetine treated adult rats (paired t-test p=0.703 for B and p=0.354 for C n=5). (D) Binocularity (OD) recovery in adult amblyopic rats after repeated fluoxetine administration. The C/I VEP ratio was significantly higher (t-test p<0.002 n=5) in the visual cortex of fluoxetine treated adult rats (C/I VEP ratio 2.25±0.17), compared to controls (C/I VEP ratio 1.11±0.20), and in the range of adult animals with normal vision. Error bars represent S.E.M. * statistical significance.

FIG. 2. BDNF protein expression after antidepressant treatment. Expression of BDNF, quantified by means of ELISA, was significantly higher in the visual cortex (t-test p<0.04 n=6) (A) and hippocampus (t-test p<0.01 n=6) (B) of adult rats repeatedly treated with fluoxetine than in control animals. Error bars represent S.E.M. * statistical significance. (C) Intracortical administration of BDNF. Adult animals cortically infused with BDNF showed an OD shift in the visual cortex contralateral to the deprived eye compared to controls (t-test P<0.001, n=4). Error bars represent S.E.M. * indicates statistical significance.

FIG. 3. Reduced intracortical inhibition and increased expression of BDNF in the adult rat visual cortex after repeated antidepressant treatment. (A) Brain microdialysis in the visual cortex of fluoxetine treated adult rats. Basal extracellular levels of GABA were significantly lower in fluoxetine treated animals than in controls (two-ways ANOVA repeated measures p=0.02 post hoc Holm-Sidak test p<0.02 n=5). (B) Long-term potentiation (LTP) of neural transmission in the adult visual cortex. LTP after theta-burst stimulation (TBS) from the white matter (WM-LTP), measured 20-30 min following TBS, was significantly enhanced in the visual cortex of fluoxetine treated animals compared to control rats (two-ways ANOVA repeated measures p<0.005 post hoc Student-Newman-Keuls test p<0.01). Scale bars are 50% of baseline amplitude and 5 ms. (C and D): Cortical administration of diazepam prevented the restoration of OD plasticity induced by chronic fluoxetine administration. (C) Schematic diagrams of the experimental procedure followed (top) and of the osmotic minipump implant and recording site of VEPs in the binocular visual cortex contralateral to the deprive eye (bottom). Cortical administration of the benzodiazepine agonist diazepam (Dz) was performed in parallel with MD during the last week of antidepressant treatment. (D) Blockade of OD plasticity in fluoxetine treated rats intracortically infused with Dz. The C/I VEP ratio in the visual cortex contralateral to the deprived eye after MD in fluoxetine treated adult animals that were cortically infused with the benzodiazepine agonist diazepam (Fluox+Dz) was not different from that of control (not deprived) animals (C/I VEP ratio 2.48±0.29 t-test P=0.483, n=4) but it differed significantly from either that of adult rats chronically treated with fluoxetine (Fluox) (t-test P=0.001, n=5) and that of animals cortically infused with vehicle solution (Fluox+Veh) (t-test P=0.01, n=3). Error bars represent S.E.M. * indicates statistical significance.

DETAILED DESCRIPTION OF THE INVENTION

The present invention relates to the treatment or alleviation of amblyopia with molecules which alleviate depression, increase the cortical expression of BDNF or reduce cortical inhibition in humans. The present invention further relates to methods which alleviate amblyopia by combining such treatments with a rehabilitation treatment.

Consequently, an object of the present invention is a method for treating a human having passed the critical period of postnatal visual development with amblyopia comprising administering to the said human an effective amount of at least one drug demonstrated to alleviate symptoms of depression (antidepressant drug) in humans.

The method involves preferably a peroral administration of at least one antidepressant drug to the amblyopic subject. In the preferred embodiment of the invention, the method according to the invention also comprises a rehabilitation treatment which supports or encourages the use of the amblyopic eye.

Another object of this invention is the use of an antidepressant drug for the manufacture of a medicament for treating or alleviating amblyopia, preferably in combination with a rehabilitation treatment, in a human having passed the critical period of postnatal visual development.

The invention is based on the observation that certain drugs, which are known to have clinical antidepressant activity when administered to depressed patients, when administered to adult rats, induce plastic changes in the visual cortex, which lead to similar functional consequences as those observed in developing visual system during the developmental critical periods (see Experimental part). Such antidepressant drugs include, but are not limited to, reuptake inhibitors, such as tricyclic antidepressants, serotonin selective reuptake inhibitors (SSRI), norepinephrine (NE) selective reuptake inhibitors (NSRI) and serotonin-norepinephrine reuptake inhibitors (SNRI). Preferred antidepressant drugs for use in the method according to the invention are selected from the group consisting of SSRIs. Among preferred SSRIs may be mentioned for example fluoxetine, fluvoxamine, paroxetine, sertraline, citalopram and escitalopram, especially fluoxetine. Among SSRIs may be mentioned for example duloxetine, venlafaxine, desvenlafaxine, bicifadine and mirtazapine.

In addition to the known antidepressant drugs, also other compounds and medicaments which increase the levels of brain-derived neurotrophic factor (BDNF) in cerebral cortex can be used for treating or alleviating amblyopia in human having passed the critical period of postnatal visual development, preferably in combination with a rehabilitation treatment.

The present invention thus further relates to methods for the treatment or alleviation of amblyopia with molecules which increase the expression level of BDNF in the cerebral cortex or reduce the GABA mediated inhibition in the cortex, preferably when used in combination with a rehabilitation treatment, in humans having passed the critical period of postnatal visual development.

A further object of the invention is the use of compounds which increase the level of BDNF or reduce the GABA mediated inhibition in the cerebral cortex, for the manufacture of medicaments for treating or alleviating amblyopia in humans who have passed the critical period of postnatal visual development.

It is well established both in rats, monkeys and humans that closure of a single eye (monocular deprivation, MD) for a relatively short period (for example, a week) during the critical developmental period produces a drastic rearrangement in the innervation and function of the visual cortex such that the open eye becomes dominant at the expense of the closed eye (Berardi et al., 2003). This rearrangement is reflected as a dramatic reduction in the visual acuity of the closed eye, and can be observed in rats by using electrophysiological or behavioural measures (see Experimental part). Similarly, it is well established that in the same species, a comparable MD in adults after the closure of the critical period does not produce any discernible rearrangements. Functionally, this lack of rearrangement in adult is reflected as lack of changes in vision of either closed or open eye during the period of MD. However, as described in Experimental part, when adult rats are treated with fluoxetine for 4 weeks and subjected to MD during the last week of the treatment, a dramatic shift in favour to the open eye is observed in the visual cortex. This shift is qualitatively similar to that observed in young MD rats at the height of the critical period, since it was produced by a reduction of the response to stimulation of the deprived eye with no difference in the responsiveness to the stimulation of the open eye. Treatment of adult rats with fluoxetine alone, without a deprivation of one eye, did not produce any changes in the responsiveness of either eye to visual stimulation, suggesting that the antidepressant drug treatment reinstates the critical period plasticity in the visual cortex, but a visual deprivation of one eye is required to produce a shift in binocularity in the visual cortex. Furthermore, fluoxetine alone did not influence the orientation selectivity or cell responsiveness in the visual cortex.

If the eye subjected to MD is opened during the critical period, a partial or full recovery ensues and a reverse suture (reopening of the deprived eye while suturing shut the previously open eye) produces a rearrangement favouring the previously deprived, but now open eye. In humans, this corresponds to the prevention of the development of amblyopia in children through patching of the better eye during the critical period. However, if the MD extends beyond the end of the critical period and the closed eye is opened only in adulthood, no functional recovery or improved visual acuity can be observed. Similarly, reverse suture does not produce functional or anatomical changes. Clinically, this observation in experimental animals correlates with the development of a permanent amblyopia, if the MD or imbalanced use of eyes is not treated by eye occlusion paradigms before the end of the critical period. However, as demonstrated in Experimental part, if adult rats which have been subjected to MD early in development (postnatal day 21) are treated with fluoxetine perorally for 4 weeks with a dose which produces fluoxetine plasma levels similar to those seen in humans treated with fluoxetine for depression, and during the last two weeks of treatment are subjected to the reverse suture, there is a dramatic shift towards the eye which was closed during development but opened during the drug treatment. More importantly, the visual acuity of the opened eye is regained and binocularity is restored. These observations suggest that the antidepressant fluoxetine induces a reopening of the developmental critical period in adult mammals and enables functional reorganization within the visual cortex comparable to those occurring at the height of the critical period.

Long-term potentiation (LTP) indicates a long-lasting increase in the synaptic strength between two neurons resulting from a short strong stimulation of the particular synaptic connection and it is considered as an experimental model of neuronal plasticity and memory. Stimulation of the thalamic input fibers entering the visual cortex in the white matter by a so called theta burst stimulation paradigm readily induces an LTP in an immature visual cortex (WM-LTP) but fails to induce an LTP in adult visual cortex (Artola and Singer, 1987; Kirkwood and Bear, 1994). The disappearance of the inducibility of the WM-LTP correlates with the end of the critical period of visual plasticity. Enhanced inhibitory control by the local GABA-containing interneurons is considered as at least one mechanism which regulates the end of the critical period and disappearance of the WM-LTP response.

BDNF has been shown to be a critical regulator of neuronal plasticity. Antidepressant drugs have been shown to increase the levels of BDNF and its mRNA in the hippocampus and BDNF signalling has been shown to be critical for the behavioral effects of antidepressant drugs in rodents (Castren, 2004). As shown in the Experimental part, 3 week treatment with fluoxetine increases BDNF levels also in the visual cortex. Furthermore, infusion of BDNF into the visual cortex induces a similar reactivation in critical period plasticity as that is observed after the peroral treatment with fluoxetine, which indicates that increased BDNF expression may mediate the plasticity-enhancing effects of fluoxetine in visual cortex.

GABA-mediated cortical inhibition increases and matures during the postnatal development. It has been demonstrated that this increase in cortical inhibition critically contributes to the closure of the critical period. Cortical GABA content increases towards the end of the critical period and if this increase in GABA is prevented, the critical period remains open. Conversely, as demonstrated in the Experimental part, 3 week peroral administration of fluoxetine leads to the reduction of cortical extracellular GABA levels which leads to the reactivation of the critical period plasticity in the visual cortex. If cortical GABA signalling is artificially increased by intracortical infusion of GABA-A receptor enhancer diazepam during the peroral administration of fluoxetine, enhanced plasticity in the adult visual cortex is prevented.

The present invention relates to the use of antidepressant drugs to improve a vision of the amblyopic eye after the closure of the critical period of postnatal visual development. The present invention also relates to the combination of occlusion treatment and drug treatment with antidepressants. Amblyopia can be reduced or prevented in childhood during the developmental critical period, if the dominant eye is penalized by preventing or reducing its vision either physically or pharmacologically (Holmes and Clarke, 2006). It is known that occlusion treatments are not effective in humans after the age of about 10 years. There are no reports of enhanced vision of the amblyopic eye in human having passed the critical period of postnatal visual development taking antidepressants for mood disorders, which is not surprising, since occlusion treatments are required for the prevention or amblyopia in the childhood. As shown in Experimental part, occlusion (reverse suture) in rats, which have developed amblyopia due to MD since early postnatal life, when combined with repeated peroral treatment with fluoxetine, is able to bring about similar changes as occlusion procedures do during the height of the critical period. It is therefore proposed that a combination of antidepressant drug treatment with specific measures of rehabilitation, such as optical (patching) or pharmacological (topical atropine eye drop) penalization of the dominant eye, will be required for the improvement in adulthood.

The antidepressant drug can be administered to a mammal suffering from amblyopia prior to, at the same time or both prior to and simultaneously of the application of any means which support or encourage the use of the amblyopic eye (rehabilitation treatment). Because clinically relevant effect of antidepressant drugs in depressed human patients occurs with a delay of several weeks, preferably, the antidepressant drug is also in the case of amblyopia administered repeatedly for a period of several weeks before the commencement of the occlusion therapy. The total duration of the drug treatment will depend on the clinical response achieved, but it is to be expected that changes will not take place as rapidly as was observed in rats in the Experimental part (within one week), but that a treatment or the combination of treatment and rehabilitation will need to be administered for a longer period of time, for example, a year. It may also be possible to combine a continuous drug treatment with a periodic occlusion therapy, or both drug treatment and the occlusion may be given for a shorter period and then repeated later for a number of times until a desirable response is obtained. It is, however, not expected that the treatment need to be given life-long, but a stabile clinical response achieved during the treatment will persist also after the cessation of the antidepressant treatment or the combination of the antidepressant and occlusion treatment.

The antidepressant drug can be administered in the form of a pharmaceutical composition adapted for oral administration. In the Experimental part, a significant improvement in visual acuity was achieved by a treatment of fluoxetine which yields plasma concentrations of about 350 ng/ml, which is within the therapeutic range of fluoxetine plasma concentrations recommended for the treatment of depression (50-450 ng/ml). Therefore, the dose of the antidepressant drug administered is expected to be at least at the level of that recommended for the treatment of depression.

According to the invention, the composition administered to a subject in need of treatment of amblyopia comprises a pharmaceutically acceptable carrier and at least one selected antidepressant drug or another drug able to increase BDNF levels or decrease GABA levels in the visual cortex. The concentration of the antidepressant drug in the composition depends on the type of antidepressant and on the pharmaceutical formulation. It is to be expected that pharmaceutical formulations currently being used for the peroral treatment of depression can be used for the treatment of amblyopia.

The present invention is further described in the following example. The example is not to be construed as limiting the scope of the claims.

Experimental part. Antidepressant drug fluoxetine induces functional reorganisation in response to monocular deprivation in adult rat visual cortex 1.1. Materials and Methods
1.1.1. Animal Treatment Adult Long-Evans hooded rats were used in this study. Animals were group-housed under standard conditions with food and water ad libitum in plexiglass cages (40×30×20 cm) and kept in a 12:12 light/dark cycle.

Fluoxetine Administration

Adult rats at the postnatal day (P) 70 were systemically treated with fluoxetine (0.2 mg ml$^{-1}$ drinking water) (Fluoxetine-hydrochloride, Galeno, Prato-Italy) during 4 weeks. Control animals were housed under the same standard conditions except for fluoxetine administration. This method of administration yields steady-state plasma concentrations of 356±99 ng/ml in rats, which is within the recommended plasma concentration for the treatment of depression in humans (50-450 ng/ml).

Monocular Deprivation (MD)

To assess ocular dominance plasticity, one week of monocular deprivation (MD) was performed through eyelid suturing at the beginning of the third week of repeated fluoxetine (P90) or vehicle administration. Adult animals, under treatment, were anesthetized with avertin (1 ml kg$^{-1}$) and mounted on a stereotaxic apparatus to be monocularly deprived. Eyelid closure was inspected daily until complete cicatrization; subjects with even minimal spontaneous re-opening were excluded. Great care was taken during the first days after MD to prevent inflammation or infection of the deprived eye through topical application of antibiotic and cortisone.

To perform analysis of long-term MD, rats were anesthetized with avertin (1 ml kg$^{-1}$) and monocularly deprived through eyelid suturing at P21. Eyelid closure was inspected daily until complete cicatrization; subjects with even minimal spontaneous re-opening were excluded. Adult amblyopic rats were then subjected to reverse suture (RS), under anesthesia, at the beginning of the second week (P85) of repeated fluoxetine or vehicle administration. The long-term deprived eye was re-opened using thin scissors, while the other eye was sutured shut. Great care was taken during the first days after RS to prevent inflammation or infection in the previously deprived eye through topical application of antibiotic and cortisone.

1.1.2. Assessment of Functional Changes
In Vivo Electrophysiology, Ocular Dominance Plasticity and Visual Acuity At the end of repeated fluoxetine administration adult animals (P100), monocularly deprived for one week, were anesthetized with urethane (0.7 ml kg$^{-1}$; 20% solution in saline; Sigma) by i.p. injection and placed in a stereotaxic frame. Additional doses of urethane were used to keep the anesthesia level stable throughout the experiment. Body temperature was continuously monitored and maintained at ~37° C. by a thermostated electric blanket during the experiment. An ECG was continuously monitored. A hole was drilled in the skull, corresponding to the binocular portion of the primary visual cortex (binocular area Oc1B) contralateral to the deprived eye. After exposure of the brain surface, the dura was removed, and a micropipette (2 MΩ) filled with NaCl (3 M) was inserted into the cortex 5 mm from λ (intersection between sagittal- and lambdoid-sutures). Both eyes were fixed and kept open by means of adjustable metal rings surrounding the external portion of the eye bulb. We measured visual acuity through both eyes using visual evoked potentials (VEPs). During recording through one eye, the other was covered by a black adhesive tape. To record VEPs, the electrode was advanced at a depth of 100 or 400 μm within the cortex. At these depths, VEPs had their maximal amplitude. Signals were band-pass-filtered (0.1-100 Hz), amplified, and fed to a computer for analysis, as described previously (Huang et al., 1999). Briefly, at least 128 events were averaged in synchrony with the stimulus contrast reversal. Transient VEPs in response to abrupt contrast reversal (0.5 Hz) were evaluated in the time domain by measuring the peak-to-baseline amplitude and peak latency of the major negative component. Visual stimuli were horizontal sinusoidal gratings of different spatial frequencies and contrast, generated by a VSG2/2 card running custom software and presented on a monitor (20×22 cm; luminance 15 cd m$^{-2}$) positioned 20 cm from the rat's eyes and centred on the previously determined receptive fields. Visual acuity was obtained by extrapolation to zero amplitude of the linear regression through the last four to five data points in a curve where VEP amplitude is plotted against log spatial frequency. Binocularity (ocular dominance) was assessed calculating the contralateral to ipsilateral (C/I) VEP ratio, i.e. the ratio of VEP amplitudes recorded by stimulating the eye respectively contralateral and ipsilateral to the visual cortex where recording is performed.

Behavioral Assessment of Visual Acuity

We measured visual acuity of the open eye (not deprived) before performing RS, so that behavioral assessment of visual acuity for the normal eye in long-term monocularly deprived rats (P70) started at the beginning of treatment with fluoxetine. Then, after RS, during the third week of treatment (P90), we started measuring visual acuity of the long term deprived eye. Therefore, visual acuity measurement of the formerly deprived eye was completed when animals were about P100, at the end of repeated fluoxetine administration. To measure visual acuity, we used the visual water task (Prusky et al., 2000) which trains animals to first distinguish a low (0.1 cycles per degree (c deg$^{-1}$)) spatial frequency vertical grating from grey, and then tests the limit of this ability at higher spatial frequencies. The apparatus consists of a trapezoidal-shaped pool with two panels placed side by side at one end. A midline divider is extended from the wide end of the pool into the middle, creating a maze with a stem and two arms. The length of the divider sets the choice point and effective spatial frequency. An escape platform is placed below the grating. Animals are released from the centre at the end of the pool opposite the panels. The position of the grating and the platform is alternated in a pseudorandom sequence over training trials while the rats are shaped to swim towards the grating in one of the maze arms. A trial is recorded as incorrect if an animal enters the arm without the platform. Animals are removed from the pool when they find the platform. Once 80% accuracy is achieved, the limit of the discrimination is estimated by increasing the spatial frequency of the grating. Visual acuity has been taken as the spatial frequency corresponding to 70% of correct choices on the sigmoidal function fitting the psychometric function. During each session, the experimenter was blind to the experimental group.

1.1.3. Assessment of Biochemical Changes
In Vivo Brain Microdialysis

One week before the initiation of the repeated fluoxetine administration, adult rats (P70) were anesthetized and stereotaxically implanted with stainless steel guide shaft above the binocular visual cortex (binocular area Oc1B), at coordinates: 7.3 mm posterior to bregma, 4.4 mm lateral to the midsagittal suture and 1 mm ventral to the skull. After the end of repeated treatment with fluoxetine, the in vivo sampling of dialysates was performed inserting a microdialysis probe into the guide shaft previously implanted. A detailed description of the procedure followed is reported in (Hernandez et al., 1986). Briefly, the probe was made of concentric fused-silica polyimide covered capillary tube into a 26 gauge stainless steel tube with a 1 mm long tip of exposed cellulose membrane (6000 MW cut-off). It was connected to a dialysis system pumping an artificial CSF (142 mM NaCl, 3.9 mM KCl, 1.2 mM $CaCl_2$, 1 mM $MgCl_2$, 1.35 mM $Na_2HPO_4$, pH 7.4) at a flow rate of 1 μl min$^{-1}$. The probe protruded 1 mm from the tip of the guide shaft. Six hours after insertion of the probe (stabilization period), sampling was carried out. Six samples (20 μl/each) were collected every 20 min along 2 hours for each freely moving fluoxetine treated and control animal.

Histology

After brain microdialysis, rats were sacrificed with an overdose of chloral hydrate and perfused intracardially as described above. Brains were post-fixed for two hours before being immersed in 30% sucrose in PBS. Forty (40) μm coronal sections from the occipital cortex were cut on a sledge microtome and collected in PBS. Brain sections were then stained for cresyl violet to verify probes' location in OclB. Only those animals with a correct location of the probe were taken into account for further analysis.

High Performance Liquid Chromatography (HPLC)

Analysis of γ-aminobutyric acid (GABA) and glutamate (GLU) basal levels from microdialysates was performed using High Performance Liquid Chromatography (HPLC) coupled to a fluorimetric detection system. A sample automatic derivatization (Waters 2690 Alliance) with o-phthalaldehyde was followed (Calabresi et al., 1995). Resolution was obtained through a C18 reverse phase chromatographic column coupled to the fluorimetric detection (Waters 474; excitation wavelength 350 nm, emission wavelength recorder 450 nm). Buffer and gradient program was as follows: by definition, solvent A: 0.1M Sodium Acetate pH 5.8/methanol 20/80; solvent B: 0.1M Sodium Acetate pH 5.8/methanol 80/20; solvent C: 0.1M Sodium Acetate pH 6.0/methanol 80/20. Concerning the gradient program, initial isocratic step 5% A, 95% C from 0 to 5 min; 15% A, 85% B from 4 to 5 min and then isocratic until 9 min; 22% A, 66% B until 14.5 min and then 34% A, 66% B until 17 min; 5% A, 95% C until 19 min and then isocratic until 23 min. Flow rate was 0.9 ml min$^{-1}$. Homoserine was used as internal standard and amino-acid concentrations were calculated from a linear standard curve built upon known concentrations of injected amino acids. Area of the peaks were used to make comparisons (Waters Millenium 32).

LTP Recordings

Brains from fluoxetine treated and control adult rats (P100) were removed and immersed in ice-cold cutting solution containing (in mM): 220 sucrose, 3.1 KCl, 1.0 K$_2$HPO$_4$, 4.0 NaHCO$_3$, 2.0 MgCl$_2$, 1.0 CaCl$_2$, 10 HEPES, 1.0 ascorbic acid, 0.5 myo-Inositol, 2.0 pyruvic acid, and 1.0 kynurenate, pH 7.3. Slices (0.35 mm thick) of visual cortex were obtained using a Leica (Nussloch, Germany) vibratome. Slices (n=12 slices for fluoxetine treated animals and n=14 slices for controls) were then perfused at a rate of 2 ml min$^{-1}$ with 35° C. oxygenated recording solution. The recording solution was composed as the cutting solution with the following differences (in mM): 130 NaCl, 5.0 dextrose, 1.0 MgCl2, 2.0 CaCl$_2$, 0.01 glycine, no kynurenate, no sucrose. Electrical stimulation (100 μsec duration) was delivered with a bipolar concentric stimulating electrode (FHC, St. Bowdoinham, Me.) placed at the border of the white matter and layer VI. Field potentials in layers II-III were recorded by a micropipette (1-3MΩ) filled with NaCl (3 M). Baseline responses were obtained every 30 sec with a stimulation intensity that yielded a half-maximal response. After achievement of a 15 min stable baseline (field potential amplitude within 15% of change and with no evident increasing or decreasing trends), θ burst stimulation (TBS) was delivered. Postsynaptic field potentials after TBS were recorded every 30 sec during 30 min.

Enzyme Linked ImmunoSorbent Assay (ELISA)

The expression of BDNF protein was assessed at the end of repeated fluoxetine administration using the ELISA assay. Proteins from fresh visual cortex and hippocampus were initially extracted, respectively, using lysis buffer (1% Triton X-100, 10% Glycerol, 20 mM TrisHCl pH 7.5, 150 mM NaCl, 10 mM EDTA, 0.1 mM Na3VO4, 1¼ g/ml Leupeptin, 1¼ g/ml Aprotinin, 1 mM PMSF). The total concentration of samples was quantified with the protein assay kit (Bio-Rad, Hercules, Calif.) using a BSA based standard curve. Afterwards, BDNF expression was assessed loading 100 μg of total proteins in triplicate in a standard ELISA plate together with a standard curve and processed as indicated in the manufacturer protocol (BDNF, Promega).

1.1.4. Intracortical administration of BDNF.

A different group of adult rats (n=4) was intracortically infused with BDNF during one week of MD. An osmotic minipump connected via PE tubing to a stainless steel cannula (30 gauge), was implanted in the visual cortex contralateral to the deprived eye. Osmotic minipumps (flow rate, 0.5 μl hr$^{-1}$) were filled up with BDNF (1 ng μl$^{-1}$). Soon after surgery, rats were transferred to standard condition cages. Electrophysiological recording of the C/I ratio by VEPs was performed, as previously described, after one week of BDNF cortical administration. BDNF at this concentration (1 ng μl$^{-1}$) was previously shown to diffuse 1.2 mm lateral from the infusion site (4.5 mm from λ). To prevent sampling bias, VEPs were recorded at three different penetrations within the diffusion area of BDNF in Oclb (4.9; 5.0; 5.1 mm lateral from λ). VEP recordings were performed at 100 μm and 400 μm depth for each penetration.

1.1.5. Intracortical Infusion of the Benzodiazepine Diazepam.

At the beginning of the last week of chronic treatment with fluoxetine (Day 21 of treatment), a different group of adult rats was subjected to MD. In parallel, under anesthesia, an osmotic minipump connected via PE tubing to a stainless steel cannula (30 gauge), was implanted in the visual cortex contralateral to the deprived eye. Osmotic minipumps (flow rate, 0.5 μl hr$^{-1}$) were filled up with the benzodiazepine agonist diazepam (DZ; 2 mg ml$^{-1}$; n=4) or vehicle solution (50% propylene glycol; n=4). Soon after surgery, rats were transferred to standard condition cages and kept under fluoxetine treatment for one more week. Electrophysiological recording of the C/I ratio by VEPs was performed at the end of antidepressant treatment as previously described.

Figure 1:
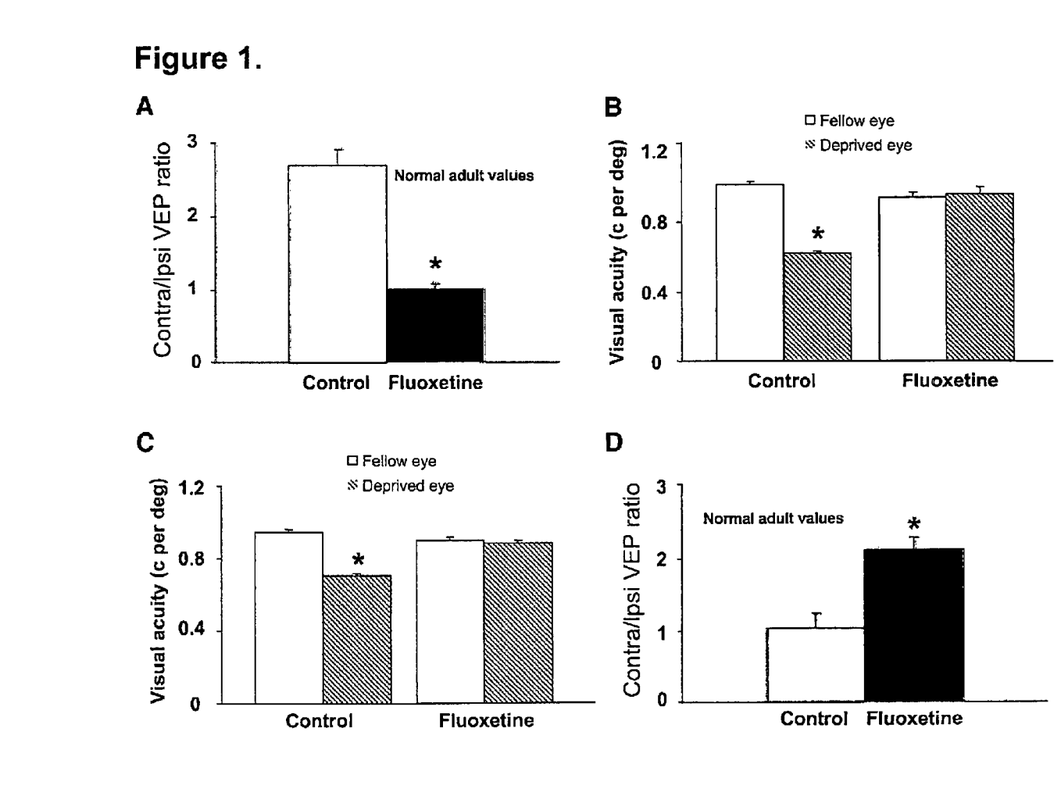

1.2. Results 1.2.1. Reactivation of Ocular Dominance (OD) Plasticity in the Adult Visual Cortex after Repeated Peroral Fluoxetine Administration We initially investigated the effects of one week of monocular deprivation (MID) on the ocular dominance (OD) plasticity of adult animals repeatedly treated with fluoxetine, by recording visual evoked potentials (VEPs) in the binocular region of the primary visual cortex contralateral to the deprived eye. VEPs represent the integrated response of a population of neurons to patterned visual stimuli and are routinely used to evaluate visual acuity (VA) and binocularity alterations (Huang et al, 1999; Porciatti et al, 1999). We assessed OD (binocularity) calculating the contralateral to ipsilateral (C/I) VEP ratio, i.e. the ratio of VEP amplitudes recorded by stimulating the eye contralateral and ipsilateral, respectively, to the visual cortex where recording is performed. The C/I VEP ratio is around 2.5 in adult animals, reflecting the predominance of crossed fibres in the rat retinal projections. MD in control animals did not change binocularity in the visual cortex contralateral to the deprived eye (CA VEP ratio 2.73±0.2 n=5). In contrast, fluoxetine treated adult rats showed a marked OD shift in favor of the non deprived eye after MD (C/I VEP ratio 1.0±0.08 t-test p<0.001 n=5) (FIG. 1A), thus displaying a plastic modification that is normally restricted to early stages of brain development.

1.2.2. Recovery of Visual Functions in Adult Amblyopic Rats after Repeated Peroral Fluoxetine Administration To further assess the effects induced by repeated treatment with fluoxetine on visual cortical plasticity we next evaluated the recovery of visual functions in adult rats that were rendered amblyopic by long-term MD and then reversed-sutured (RS) during the last two weeks of antidepressant treatment (see methods). We measured VA recording VEPs from the VC contralateral to the long-term deprived eye. In control animals, VA of the formerly deprived eye did not show any sign of recovery (0.62±0.06 c deg$^{-1}$) compared to the fellow eye (1.06±0.01 c deg$^{-1}$) (FIG. 1B). In contrast, fluoxetine treated adult rats showed complete rescue of VA (0.97±0.04 c deg$^{-1}$). Behavioral measure (visual water box task) of VA, in the same animals in which we recorded VEPs, confirmed the electrophysiological data: complete recovery of VA (0.88±0.02 c deg$^{-1}$) was evident in fluoxetine treated long-term deprived rats but not in controls (FIG. 1C). In the same animals in which VA was assessed, we also evaluated OD measuring the C/I VEP ratio. In control animals, there was no rescue of binocularity in the visual cortex contralateral to the formerly deprived eye (C/I VEP ratio=1.11±0.20) (FIG. 1D) whereas fluoxetine treated adult rats showed full recovery of binocularity with a C/I ratio of 2.25±0.17.

Figure 2:
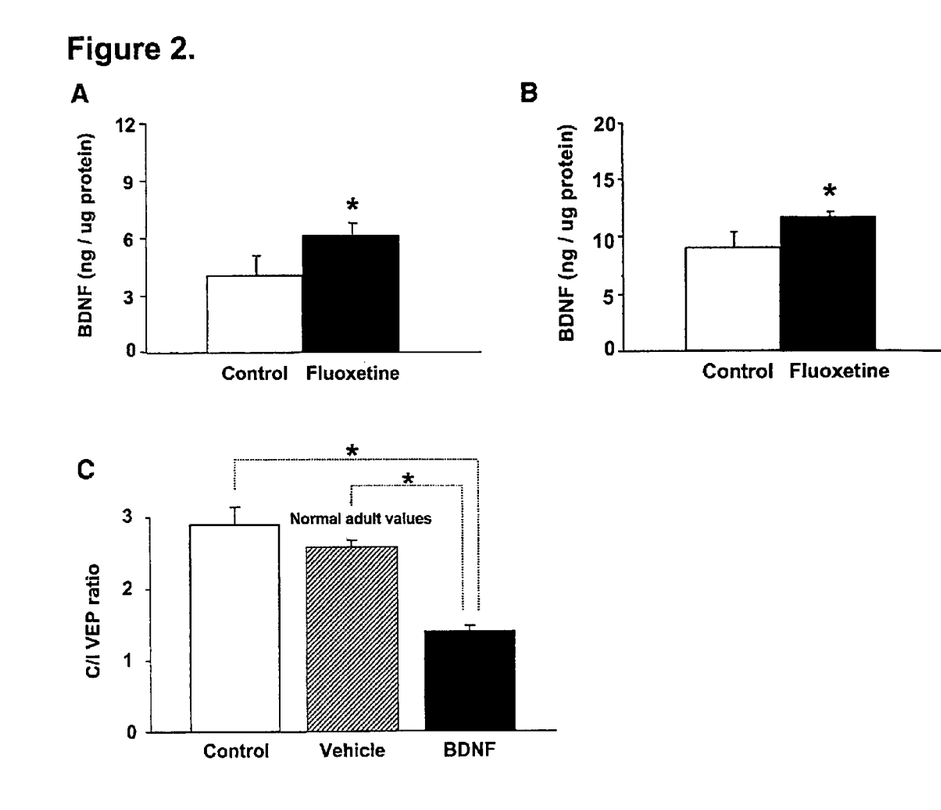

1.2.3. Effects of Repeated Peroral Fluoxetine Administration on BDNF Expression in the Adult Visual Cortex Because repeated antidepressant administration increases the expression of the neurotrophin BDNF in limbic structures, most notably in the hippocampus, (Nibuya et al., 1995; Castrén, 2004) we measured BDNF protein levels, using the ELISA method, in the adult rat visual cortex after repeated fluoxetine administration. BDNF protein expression was significantly higher in the visual cortex of fluoxetine treated adult rats compared to controls (t-test p<0.04 n=6) (FIG. 2A). BDNF protein expression was similarly enhanced in the hippocampus of fluoxetine treated adult rats relative to control animals (t-test p<0.01 n=6) (FIG. 2B). To examine whether the increased BDNF expression is causally linked to the reinstatement of plasticity in the adult visual system, we then assessed OD in rats that were intracortically infused (via osmotic minipumps) with BDNF (1 ng µl$^{-1}$) in parallel to MD. Control animals infused with vehicle solution showed no change of binocularity in the visual cortex contralateral to the deprived eye (C/I VEP ratio 2.44±0.1, n=2). In contrast, adult rats intracortically infused with BDNF showed an OD shift in response to MD (C/I VEP ratio 1.32±0.08 t-test P<0.001, n=4) (FIG. 2C).

Figure 3:
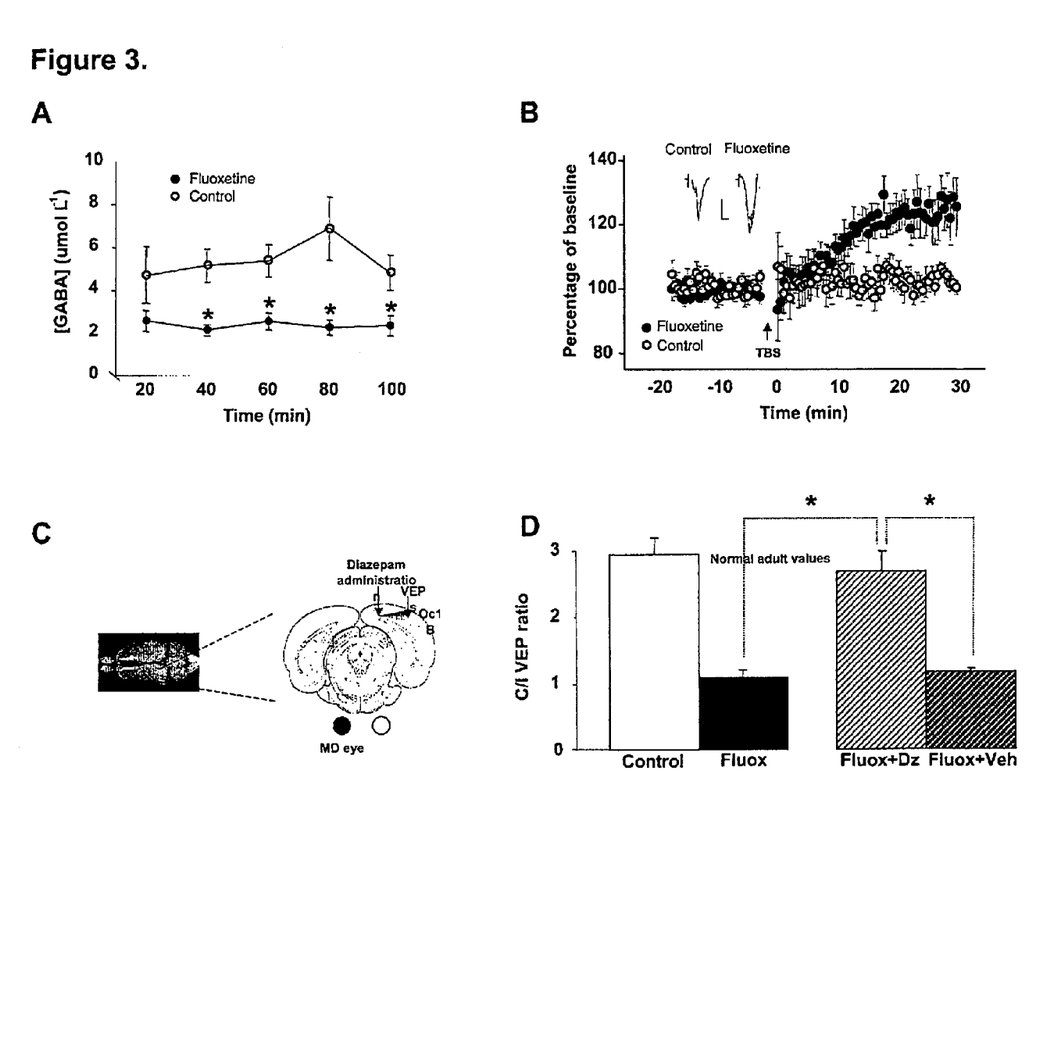

1.2.4. Effects of Repeated Peroral Fluoxetine Administration on the GABAergic Transmission in the Adult Visual Cortex We used in viva brain microdialysis to investigate whether the fluoxetine induced visual cortical plasticity was paralleled by changes in the GABAergic transmission. Quantification of extracellular basal levels of γ-aminobutyric acid (GABA) revealed a significant reduction of intracortical inhibition in the visual cortex of fluoxetine treated adult rats (FIG. 3A) compared to controls (two-ways ANOVA repeated measures p=0.02 post hoc Holm-Sidak test p<0.02 n=5). No difference in extracellular glutamate (GLU) levels was detected between fluoxetine treated and control animals (data not shown).

To further assess the reduction of intracortical inhibition we examined long-term potentiation of layer II-III field potentials after theta-burst stimulation from the white matter (WM-LTP), a form of synaptic plasticity that is absent in the adult because of the maturation of intracortical inhibitory circuitries (Artola and Singer, 1987; Kirkwood and Bear, 1994). Notably, WM-LTP was fully restored in fluoxetine treated adult rats (FIG. 3B). No WM-LTP was present in control animals.

To directly test whether the reduction of intracortical inhibition underlies the reopening of visual cortical plasticity in adulthood, we evaluated OD in fluoxetine treated adult rats that were infused intracortically with the benzodiazepine agonist diazepam (2 mg ml$^{-1}$) or vehicle solution during the period of MD (FIG. 3A). Cortical diazepam administration in adult rats chronically treated with fluoxetine totally prevented the OD shift induced by MD (FIG. 3B). Control animals intracortically infused with vehicle solution showed an OD shift in favor of the non deprived eye following MD (C/I VEP ratio 1.07±0.04 t-test P=0.01, n=3).

PATENT REFERENCES

WO 9425034 A1 (University of Pennsylvania), 1994.
WO 0152832 A1 (Valley Forge Pharmaceuticals), 2001.
WO 03032975 A1 (The Trustees of the University of Pennsylvania), 2003.
U.S. Pat. No. 5,567,731 A (Laties A., et al.), 1996.
U.S. Pat. No. 5,571,823 A (Stone R. A., et al.), 1996.
US 2003114830 A1 (Guerrero J. M.), 2003)

REFERENCES

Artola A, Singer W (1987) Long-term potentiation and NMDA receptors in rat visual cortex. Nature 330:649-652.
Berardi, N., Pizzorusso, T., Ratto, G. M., and Maffei, L. (2003). Molecular basis of plasticity in the visual cortex. Trends in Neurosciences 26, 369-378.
Calabresi P, Fedele E, Pisani A, Fontana G, Mercuri N B, Bernardi G, Raiteri M (1995) Transmitter release associated with long-term synaptic depression in rat corticostriatal slices. Eur J Neurosci 7:1889-1894.
Campos E C, Fresina M. (2006) Medical treatment of amblyopia: present state and perspectives. Strabismus. 2006 14:71-3.
Castrén, E. (2004). Neurotrophic effects of antidepressant drugs. Curr. Opin. Pharmacol. 4, 58-64.
Hernandez L, Stanley B G, Hoebel B G (1986) A small, removable microdialysis probe. Life Sci 39:2629-2637.
Holmes, J. M. and Clarke, M. P. (2006). Amblyopia. The Lancet 367, 1343-1351.
Huang Z J, Kirkwood A, Pizzorusso T, Porciatti V, Morales B, Bear M F, Maffei L, Tonegawa S (1999) BDNF regulates the maturation of inhibition and the critical period of plasticity in mouse visual cortex. Cell 98:739-755.
Kirkwood A, Bear M F (1994) Hebbian synapses in visual cortex. J Neurosci 14:1634-1645.
Nibuya M, Morinobu S, Duman R S (1995) Regulation of BDNF and trkB mRNA in rat brain by chronic electroconvulsive seizure and antidepressant drug treatments. J Neurosci 15:7539-7547.
Pizzorusso T, Medini P, Berardi N, Chierzi S, Fawcett J W, Maffei L. (2002). Reactivation of ocular dominance plasticity in the adult visual cortex. Science, 298:1248-1251.
Pizzorusso T, Medini P, Landi S, Baldini S, Berardi N, Maffei L. (2006). Structural and functional recovery from early monocular deprivation in adult rats. Proc Natl Acad Sci USA, 103:8517-8522.
Porciatti V, Pizzorusso T, Maffei L (1999) The visual physiology of the wild type mouse determined with pattern VEPs. Vision Res 39:3071-3081.
Prusky G T, West P W, Douglas R M (2000) Behavioral assessment of visual acuity in mice and rats. Vision Res 40:2201-2209.
Sale A, Maya Vetencourt J F, Medini P, Cenni M C, Baroncelli L, De Pasquale R, Maffei L (2007) Environmental enrichment in adulthood promotes amblyopia recovery through a reduction of intracortical inhibition. Nat Neurosci 10: 679-681.

The invention claimed is:
1. A method for treating or alleviating amblyopia in a human, comprising selecting an amblyopic human patient who has passed the critical period of postnatal visual development, and subsequently administering to the said amblyopic human who has passed the critical period of postnatal visual development an effective amount of at least one monoamine oxidase inhibitor (MAOI), tricyclic antidepressant, serotonin selective reuptake inhibitor (SSRI), norepinephrine selective reuptake inhibitor (NSRI), or serotonin-norepinephrine reuptake inhibitor (SNRI), wherein said administration is combined with a rehabilitation treatment for amblyopia.

2. A method for treating or alleviating amblyopia in a human, comprising selecting an amblyopic human patient who has passed the critical period of postnatal visual development, and subsequently administering to the said amblyopic human who has passed the critical period of postnatal visual development an effective amount of at least one compound demonstrated to increase the levels of Brain-derived neurotrophic factor (BDNF) in the cerebral cortex, wherein said administration is combined with a rehabilitation treatment for amblyopia.

3. The method according to claim 1 wherein the drug belongs to the class of serotonin selective reuptake inhibitors (SSRI).

4. The method according to claim 3, wherein the serotonin selective reuptake inhibitor is selected from the group consisting of fluoxetine, fluvoxamine, paroxetine, sertraline, citalopram, escitalopram, and their enantiomers.

5. The method according to claim 1, wherein the antidepressant drug is fluoxetine.

6. The method according to claim 1 or 2, wherein the recited compound is administered orally.

7. The method according to claim 1, wherein the drug is selected from the group consisting of tricyclic antidepressant reuptake inhibitors, serotonin selective reuptake inhibitors, norepinephrine selective reuptake inhibitors, and serotonin-norepinephrine reuptake inhibitors.

8. The method according to claim 7, wherein the drug belongs to the class of serotonin-norepinephrine reuptake inhibitors (SNRI).

9. The method according to claim 8, wherein the serotonin-norepinephrine reuptake inhibitor is selected from the group consisting of duloxetine, venlafaxine, desvenlafaxine, bicifadine, mirtazapine, and their enantiomers.

10. A method for treating or alleviating amblyopia in a human, comprising administering to a human suffering from amblyopia, who has passed the critical period of postnatal visual development, an effective amount of at least one compound demonstrated to increase the levels of Brain-derived neurotrophic factor (BDNF) in the cerebral cortex, and providing said human with means which supports or encourages use of the amblyopic eye.

11. A method for treating or alleviating amblyopia in a human, comprising administering to a human suffering from amblyopia, who has passed the critical period of postnatal visual development, an effective amount of at least one monoamine oxidase inhibitor (MAOI), tricyclic antidepressant reuptake inhibitor, serotonin selective reuptake inhibitor (SSRI), norepinephrine selective reuptake inhibitor (NSRI), or serotonin-norepinephrine reuptake inhibitor (SNRI), and providing said human with means which supports or encourages use of the amblyopic eye.

12. The method according to claim 10 or 11, wherein the recited compound is administered to the human prior to, at the same time, or both prior to and simultaneously with the application of the means which supports or encourages the use of the amblyopic eye.

13. The method according to claim 10 or 11, wherein continuous administration of the compound is combined with a periodic application of one or several means which support or encourage the use of the amblyopic eye.

14. The method according to claim 10 or 11, wherein the means is selected from the group consisting of physical occlusion of the vision in the better eye, pharmacological occlusion of the vision in the better eye, computer-based cognition training programs or games, and combinations thereof.

* * * * *